United States Patent
Yangdai et al.

(10) Patent No.: US 12,307,667 B2
(45) Date of Patent: May 20, 2025

(54) IMAGE PROCESSING METHOD, AND ELECTRONIC DEVICE AND READABLE STORAGE MEDIUM

(71) Applicants: ANKON TECHNOLOGIES CO., LTD, Wuhan (CN); ANX IP HOLDING PTE. LTD., Sg (SG)

(72) Inventors: Tianyi Yangdai, Wuhan (CN); Yi Li, Wuhan (CN); Hui Hu, Wuhan (CN); Hao Liu, Wuhan (CN); Fanhua Ming, Wuhan (CN)

(73) Assignees: ANKON TECHNOLOGIES CO., LTD, Wuhan (CN); ANX IP HOLDING PTE. LTD., Singapore (SG)

( * ) Notice: Subject to any disclaimer, the term of this patent is extended or adjusted under 35 U.S.C. 154(b) by 85 days.

(21) Appl. No.: 18/252,037

(22) PCT Filed: Nov. 2, 2021

(86) PCT No.: PCT/CN2021/128057
§ 371 (c)(1),
(2) Date: May 7, 2023

(87) PCT Pub. No.: WO2022/095839
PCT Pub. Date: May 12, 2022

(65) Prior Publication Data
US 2023/0419482 A1 Dec. 28, 2023

(30) Foreign Application Priority Data
Nov. 6, 2020 (CN) .......................... 202011227075.5

(51) Int. Cl.
*G06T 7/00* (2017.01)
*A61B 1/04* (2006.01)
(Continued)

(52) U.S. Cl.
CPC ............ *G06T 7/0012* (2013.01); *A61B 1/041* (2013.01); *A61B 1/045* (2013.01); *H04N 23/555* (2023.01);
(Continued)

(58) Field of Classification Search
CPC ......... G06T 7/0012; G06T 2207/10028; G06T 2207/30028; H04N 23/555; A61B 1/041; A61B 1/045
See application file for complete search history.

(56) References Cited

U.S. PATENT DOCUMENTS 10,282,857 B1  5/2019  Brailovskiy et al.
2016/0120396 A1* 5/2016  Homan .................. A61B 1/045
                                                    600/109
(Continued)

FOREIGN PATENT DOCUMENTS

CN       109410215 A    3/2009
CN       101579227 A    11/2009
(Continued)

*Primary Examiner* — Girumsew Wendmagegn
(74) *Attorney, Agent, or Firm* — Treasure IP Group, LLC (57) ABSTRACT

The present invention provides an image processing method, an electronic device, and a readable storage medium. The method comprises: obtaining an original image, determining whether the current original image contains a cavity; if the current original image contains a cavity, increasing the frame rate based on the original frame rate; if the current original image does not contain a cavity, maintaining the original frame rate for image capturing. The present invention can automatically adjust the frame rate according to the actual images captured by a capsule endoscope, improving the capture of intestinal images, reducing the probability of missing shots, and achieving the goal of saving power, while enhancing the efficiency of capsule endoscope usage.

12 Claims, 6 Drawing Sheets

(51) Int. Cl.
*A61B 1/045* (2006.01)
*H04N 23/50* (2023.01)
(52) U.S. Cl.
CPC ............... *G06T 2207/10028* (2013.01); *G06T 2207/30028* (2013.01)

(56) References Cited

U.S. PATENT DOCUMENTS

| | | |
|---|---|---|
| 2018/0343432 A1 | 11/2018 | Duan et al. |
| 2019/0208123 A1 | 7/2019 | Kawabata et al. |

FOREIGN PATENT DOCUMENTS

| | | | |
|---|---|---|---|
| CN | 103622658 | A | 3/2014 |
| CN | 108615045 | A | 10/2018 |
| CN | 110335318 | A | 10/2019 |
| CN | 110897594 | A | 3/2020 |
| CN | 110897596 | A | 3/2020 |
| CN | 111345772 | A | 6/2020 |
| JP | 2006223377 | A | 8/2006 |
| JP | 2007195586 | A | 8/2007 |
| JP | 2009240531 | A | 10/2009 |
| JP | 2010008394 | A | 1/2010 |
| JP | 2012217647 | A | 11/2012 |

\* cited by examiner

| 255 | 255 | 255 | 255 |
|-----|-----|-----|-----|
| 255 | 0   | 0   | 0   |
| 255 | 0   | 0   | 0   |
| 255 | 255 | 255 | 255 |

FIG.4

| 255 | 255 | 255 | 255 |
|-----|-----|-----|-----|
| 0   | 0   | 255 | 0   |
| 255 | 0   | 255 | 255 |
| 255 | 255 | 255 | 0   |

IMAGE PROCESSING METHOD, AND ELECTRONIC DEVICE AND READABLE STORAGE MEDIUM

CROSS-REFERENCE OF RELATED APPLICATIONS

The application is a National Phase Application of PCT International Application No. PCT/CN2021/128057, International Filing Date Nov. 2, 2021, published May 12, 2022 as International Publication Number WO2022/095839A1, which claims priority from Chinese Patent application Ser. No. 20/201,1227075.5, filed Nov. 6, 2020, all of which are incorporated herein by reference in their entirety.

FIELD OF INVENTION

The present invention relates to the field of medical device imaging, and more particularly to an image processing method, an electronic device, and readable storage medium.

BACKGROUND

An increasing number of people are using a capsule endoscope for gastrointestinal examination. The capsule endoscope is ingested by a patient, which travels through the mouth, esophagus, stomach, small intestine, and large intestine of the patient, and is finally excreted. Usually, the capsule endoscope travels passively with the peristalsis of digestive tract, and takes images at a certain frame rate during this process, so that a physician can check the conditions of various regions of the patient's digestive tract.

The capsule endoscope is powered by an internal battery and relies on a camera module to capture images of the digestive tract, which are then wirelessly transmitted outside the patient's body. Due to battery capacity limitations, the total examination time for a capsule endoscope is typically 8 to 14 hours, with a total image count of 30,000 to 100,000. As a result, the average image capture frame rate is 1 to 2 fps (frames per second), with short-term support for 4 to 8 fps, and even 10 to 30 fps.

Considering battery life, image quality, and transmission efficiency, the current capsule endoscope has the following problems:
problem 1: considering the image quality, the higher the frame rate, the smoother the video image and the lower the chance of missing shots; however, the capsule endoscope is powered by a battery with limited capacity, making it difficult to maintain at a high frame rate for 8-14 hours;
problem 2: Considering battery life, constantly capturing images at a low frame rate poses the risk of missing shots;
problem 3: there are too few images of the intestinal cavity and too many of the intestinal wall; for small intestine and colon examinations, observing the structure and morphology of the intestinal cavity is very helpful for disease diagnosis; however, when a capsule endoscope is in the intestine, the lens is likely to be close to the intestinal wall, resulting in a narrow field of view and an inability to grasp the overall situation of the intestine, which interferes with the detection of lesions.

In the current demand, it is necessary to ensure sufficient battery power, increase the frame rate, and capture more intestinal information. Therefore, a new image processing method is needed to solve the above problems.

SUMMARY OF THE INVENTION

To solve the above technical problems, it is an object of the present invention to provide an image processing method, an electronic device, and a readable storage medium.

In order to achieve the above-mentioned objects of the present invention, an embodiment of the present invention provides an image processing method, the image processing method comprises: obtaining an original image, determining whether the current original image contains a cavity; increasing a frame rate based on the original frame rate when the current original image contains a cavity; maintaining the original frame rate for image capturing when the current original image does not contain a cavity.

In an embodiment of the present invention, determining whether the current original image contains a cavity comprises:
converting the current original image into a grayscale image;
converting the grayscale image into a first binary image;
obtaining each connected region of dark pixels and counting a total quantity of connected regions with dark pixel quantity greater than a preset first quantity threshold based on the first binary image, where the dark pixels refer to the pixels with smaller grayscale values; and
determining whether the current original image contains a cavity based on the counted total quantity of connected regions of dark pixels.

In an embodiment of the present invention, converting the grayscale image to the first binary image comprises: binarizing the grayscale image based on a maximum grayscale value and a minimum grayscale value thereof to form the first binary image.

In an embodiment of the present invention, binarizing the grayscale image based on the maximum grayscale value and the minimum grayscale value thereof to form the first binary image specifically comprises:
representing the value of a pixel in the first binary image with a first value if the grayscale value of the pixel in the grayscale image is greater than the grayscale threshold; representing the value of a pixel in the first binary image with a second value if the grayscale value of the pixel in the grayscale image is not greater than the grayscale threshold, where the first value and the second value are different;
where the grayscale threshold $m1 = R \times maxv + (1-R) \times minv$, R is a coefficient of proportionality, which is a constant; maxv represents the maximum grayscale value in the grayscale image, and minv represents the minimum grayscale value in the grayscale image.

In an embodiment of the present invention, determining whether the current original image contains a cavity based on the counted total quantity of connected regions of dark pixels specifically comprises:
determining that the current original image does not contain a cavity if the total quantity of connected regions of dark pixels is 0;
determining that the current original image contains a cavity if the total quantity of connected regions of dark pixels is between 0 and a first index threshold; and
determining that the current original image is incorrectly identified if the total quantity of connected regions of dark pixels is not less than the first index threshold.

In an embodiment of the present invention, determining whether the current original image contains a cavity comprises:

converting the current original image into a depth image, where each depth value in the depth image represents a distance from an examined object corresponding to each pixel in the original image to a capsule endoscope.

converting the depth image into a second binary image;

obtaining each connected region of bright pixels and counting a total quantity of connected regions with bright pixel quantity greater than a preset second quantity threshold based on the second binary image, where the bright pixels refer to the pixels with far distance; and determining whether the current original image contains a cavity based on the counted total quantity of connected regions of bright pixels.

In an embodiment of the present invention, converting the depth image into the second binary image comprises:

representing the value of a pixel in the second binary image with a third value if the depth value of the pixel in the depth image is greater than the depth threshold;

representing the value of a pixel in the second binary image with a fourth value if the depth value of the pixel in the depth image is not greater than the depth threshold, where the third value and the fourth value are different.

In an embodiment of the present invention, determining whether the current original image contains a cavity based on the counted total quantity of connected regions of bright pixels specifically comprises:

determining that the current original image does not contain a cavity if the total quantity of connected regions of bright pixels is 0;

determining that the current original image contains a cavity if the total quantity of connected regions of bright pixels is between 0 and a second index threshold; and determining that the current original image is incorrectly identified if the total quantity of connected regions of bright pixels is not less than the second index threshold.

In an embodiment of the present invention, increasing the frame rate based on the original frame rate when the current original image contains a cavity specifically comprises:

if it is determined that the original image contains a cavity, taking a total area of the connected region used to determine the cavity as a cavity index corresponding to the original image;

adjusting the frame rate according to the cavity index, where the larger the cavity index, the higher the frame rate.

In an embodiment of the present invention, after increasing the frame rate based on the original frame rate, the method further comprises:

calculating a sampling interval time t between adjacent images according to the original frame rate;

sampling an original image at every interval time t starting from the first obtained original image; and determining whether the original image contains a cavity based on the current sampled original image after each sampling.

In an embodiment of the present invention, after determining whether the current original image contains a cavity, the method further comprises:

calculating the sampling interval time t between adjacent images according to the original frame rate;

sampling an original image at every interval time t starting from the first obtained original image; and comparing the similarity between the current sampled original image and a pre-stored image;

if the current sampled original image is similar to the pre-stored image, discarding the current original image sample; and if the current sampled original image is dissimilar to the pre-stored imaged, outputting the current sampled original image and replacing the pre-stored image with the current sampled original image.

In order to achieve one of the above-mentioned objects of the present invention, an embodiment of the present invention provides an electronic device, comprising a memory and a processor, where the memory stores a computer program that can run on the processor, and the processor executes the computer program to implement steps of the image processing method, wherein the image processing method comprises: obtaining an original image, determining whether the current original image contains a cavity; increasing a frame rate based on the original frame rate when the current original image contains a cavity; maintaining the original frame rate for image capturing when the current original image does not contain a cavity.

In order to achieve one of the above-mentioned objects of the present invention, an embodiment of the present invention provides a computer-readable storage medium, the computer-readable storage medium stores a computer program and the computer program is executed by the processor to implement steps of the image processing method, where the image processing method comprises: obtaining an original image, determining whether the current original image contains a cavity; increasing a frame rate based on the original frame rate when the current original image contains a cavity; maintaining the original frame rate for image capturing when the current original image does not contain a cavity.

According to all aspects of the present invention, the advantages over the prior art are that: the image processing method, electronic device, and readable storage medium of the present invention can automatically adjust the frame rate according to the actual images captured by the capsule endoscope, improving the capture of intestinal images, reducing the probability of missing shots, and achieving the goal of saving power, while enhancing the efficiency of capsule endoscope usage.

DETAILED DESCRIPTION

The present invention can be described in detail below with reference to the accompanying drawings and preferred embodiments. However, the embodiments are not intended to limit the invention, and the structural, method, or functional changes made by those skilled in the art in accordance with the embodiments are included in the scope of the present invention.

Figure 1:
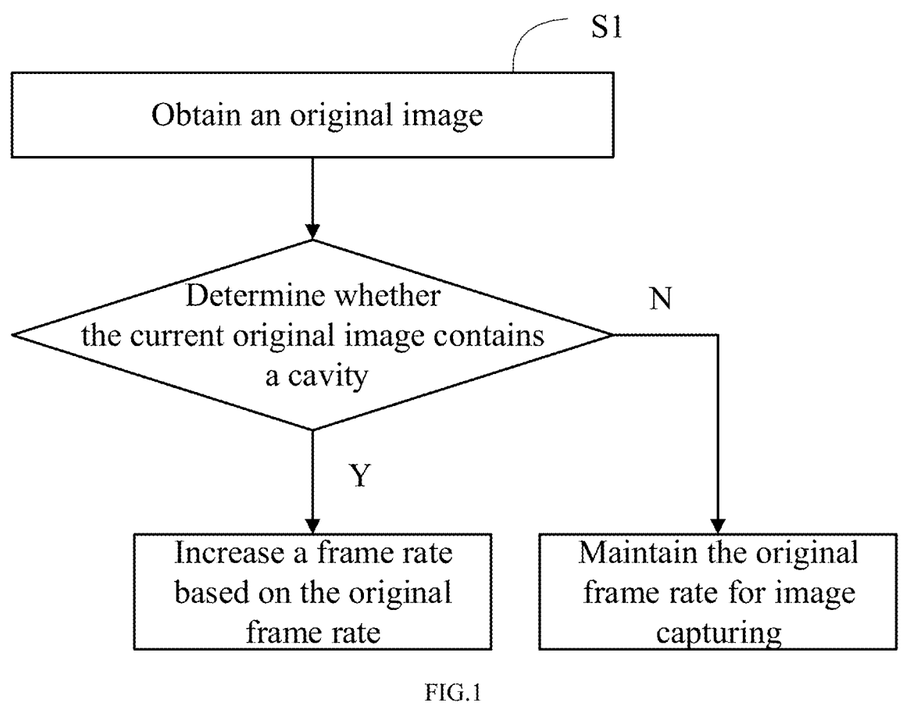
FIG. 1 shows an exemplar process flow diagram of an image processing method, in accordance with an embodiment of the present invention.

Referring to FIG. 1, an image processing method is provided in a first embodiment of the present invention, the method comprises:
step S1, obtaining an original image, determining whether the current original image contains a cavity; if the current original image contains a cavity, increasing a frame rate based on the original frame rate; if the current original image does not contain a cavity, maintaining the original frame rate for image capturing.

In a preferred embodiment of the present invention, whether the current original image contains a cavity is identified through the following two ways.

Figure 2:
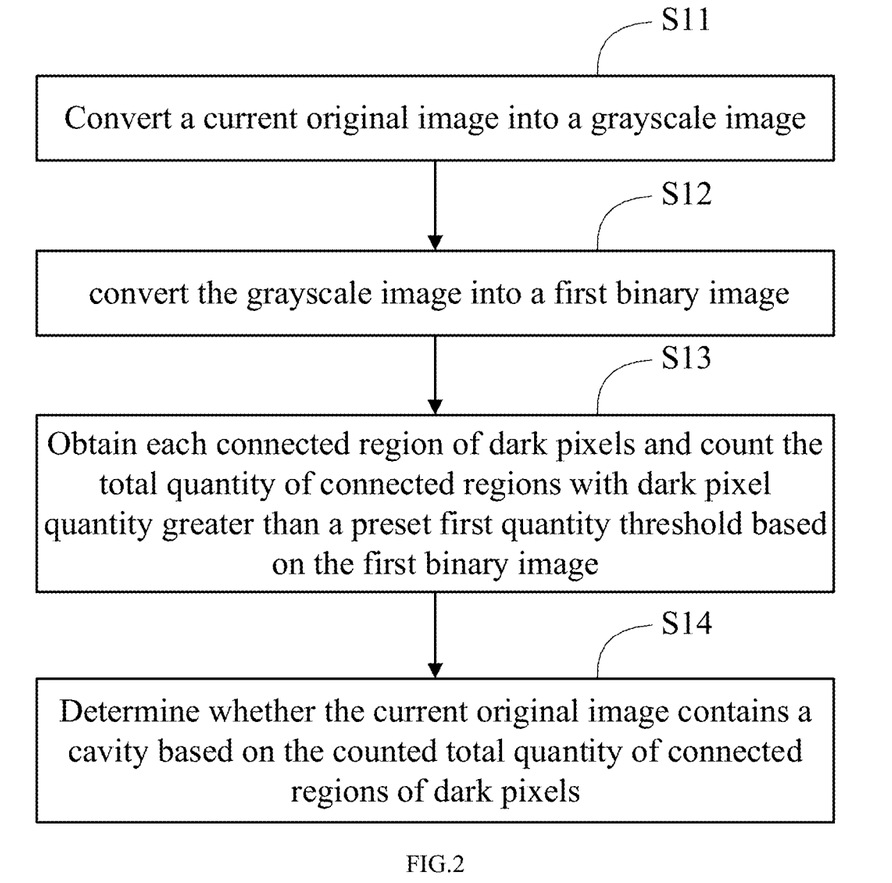
FIG. 2 shows an exemplar process flow diagram of a cavity identification based on an original image, in accordance with a first embodiment of the present invention.

In the first embodiment (method 1) of the present invention, as shown in FIG. 2, determining whether the current original image contains a cavity comprises: step S11, converting the current original image into a grayscale image; step S12, converting the grayscale image into a first binary image; step S13, obtaining each connected region of dark pixels and counting the total quantity of connected regions with dark pixel quantity greater than a preset first quantity threshold based on the first binary image, where the dark pixels refer to the pixels with smaller grayscale values; and step S14, determining whether the current original image contains a cavity based on the counted total quantity of connected regions of dark pixels.

Figure 3:
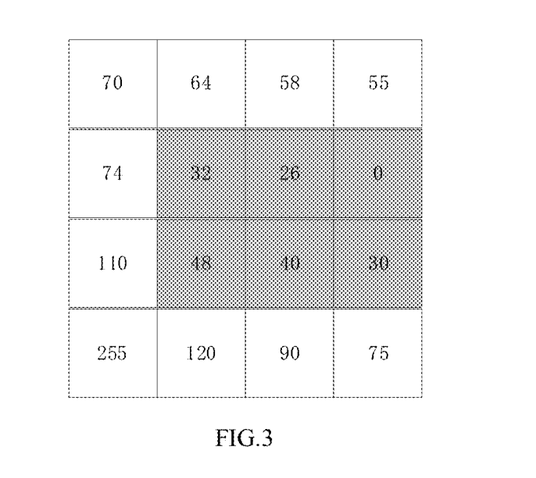
FIG. 3 shows a grayscale image of a specific embodiment of the present invention.

For step S11, the original image is a color image in RGB format, and converting the color image to the grayscale image is a prior art, and it is not further described here. Referring to FIG. 3, after the original image is converted to the grayscale image, each pixel in the grayscale image has a unique grayscale value.

Figure 4:
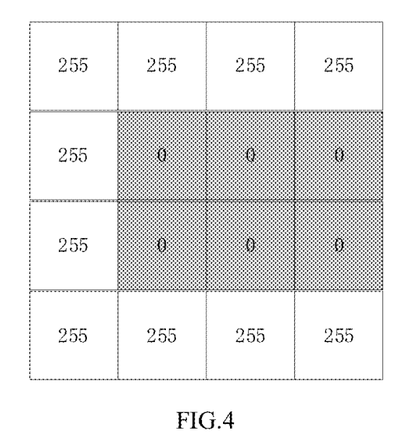
FIG. 4 shows a first binary image of a specific embodiment of the present invention.

For step S12, there are various methods to convert the grayscale image into the first binary image. In the preferred embodiment of the present invention, the first binary image is formed by binarizing the grayscale image based on the maximum grayscale value and the minimum grayscale value thereof. Specifically, calculating a grayscale threshold based on the maximum grayscale value and the minimum grayscale value; representing the value of a pixel in the first binary image with a first value if the grayscale value of the pixel in the grayscale image is greater than the grayscale threshold; representing the value of a pixel in the first binary image with a second value if the grayscale value of the pixel in the grayscale image is not greater than the grayscale threshold, where the first value and the second value are different. In a preferred embodiment of the present invention, the grayscale threshold m1 is calculated by the following formula: $m1 = R \times maxv + (1-R) \times minv$, where R is a coefficient of proportionality, which is a constant; maxv represents the maximum grayscale value in the grayscale image, and minv represents the minimum grayscale value in the grayscale image. Referring to FIG. 3, in a specific embodiment of the present invention, setting R=0.2, the grayscale image is analyzed to obtain the values of maxv and minv, resulting in: maxv=255 and minv=0. Thus, the value of m1 can be calculated by the above formula, which is 51. Further, by comparing the grayscale value of each pixel in the grayscale image with the calculated grayscale threshold m1, the first binary image as shown in FIG. 4 is formed.

It should be noted that for the first binary image, each pixel in the image is replaced with only two values. Accordingly, the two values can be specifically selected as needed. In the specific embodiment of the present invention, the two values are "0" and "255", with "0" representing dark pixels and "255" representing bright pixels. In other embodiments of the present invention, "0" and "255" can also represent bright pixels and dark pixels, respectively; and the binary values can be changed accordingly, to "0" and "1", for example, or to other values, without further elaboration.

For step S12, when taking images of the intestinal cavity, the scene has rich layers with both darker object and brighter object. Therefore, darker scenes are usually identified as the intestinal cavity, and binarizing can separate the intestinal cavity area. In this specific embodiment, values lower than the grayscale threshold are set to 0, and those higher than the threshold are set to 255.

For step S13, the quantity of dark pixels in each connected region of dark pixels is counted, and compared with the first quantity threshold to exclude discrete connected regions of dark pixels.

The first quantity threshold is a constant, and the value can be specifically set as needed.

Figure 5:
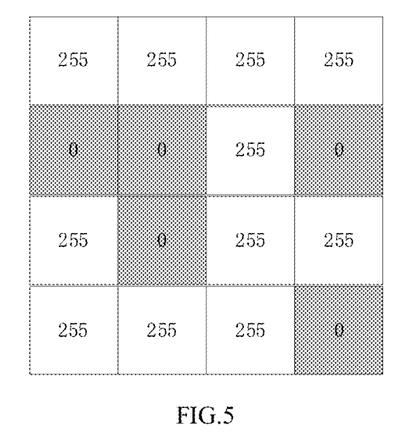
FIG. 5 shows the first binary image of another specific embodiment of the present invention.

Referring to FIG. 5, showing the first binary image of another specific embodiment of the present invention. For the specific embodiments shown in FIGS. 4 and 5, the first quantity threshold is set to 4. For the specific embodiment shown in FIG. 4, after comparison, the quantity of remaining connected regions of dark pixels used for calculation is 1. In the specific embodiment shown in FIG. 5, the quantity of pixels in each of the three connected regions of dark pixels is less than the first quantity threshold. As a result, after comparison, the quantity of remaining connected regions of dark pixels used for calculation in the specific embodiment shown in FIG. 5 is 0.

Preferably, for step S14, if the total quantity of connected regions of dark pixels is 0, it is determined that the current original image does not contain cavities; if the total quantity of connected regions of dark pixels is between 0 and a first index threshold, it is determined that the current original image contains cavities; if the total quantity of connected regions of dark pixels is not less than the first index threshold, it is determined that the current original image is incorrectly identified.

The first index threshold is a constant, and the value can be specifically set as needed. In specific embodiments of the present invention, the number of cavities in the image, if present, is usually 1, 2, or 3, and accordingly, the first index threshold is set to 4, for instance.

Figure 6:
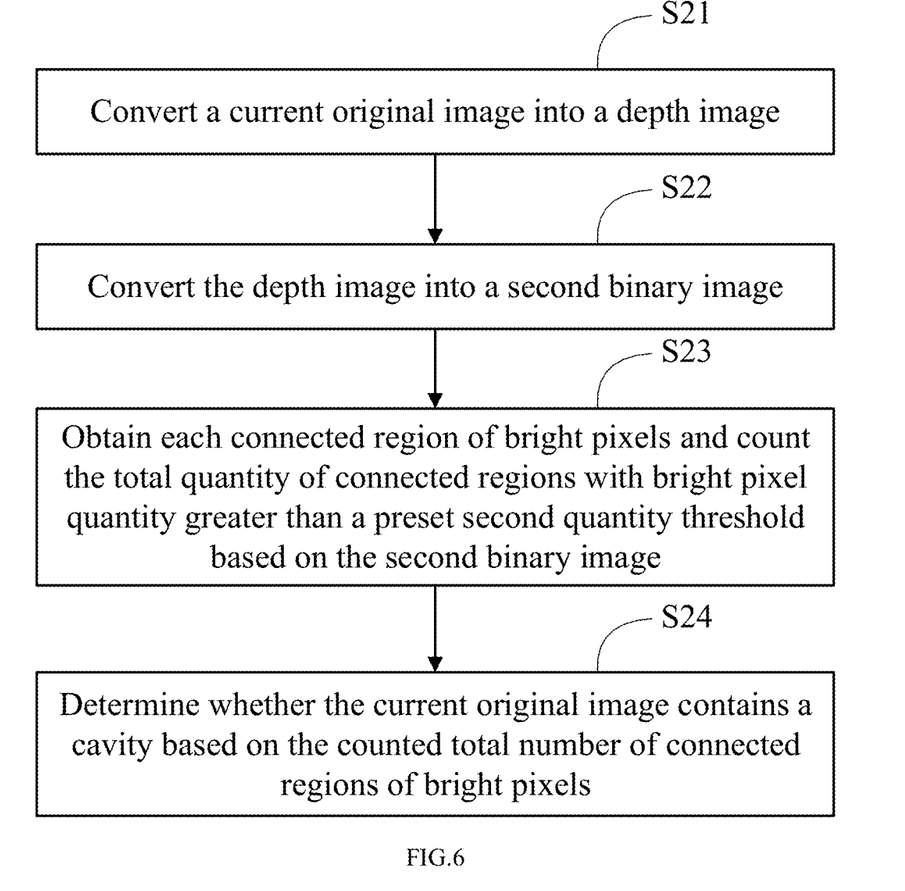
FIG. 6 shows an exemplar process flow diagram of the cavity identification based on the original image, in accordance with a second embodiment of the present invention.

Referring to FIG. 6, in the second embodiment (method 2) of the present invention, determining whether the current original image contains a cavity comprises: step S21, converting the current original image into a depth image, where each depth value in the depth image represents the distance from the examined object corresponding to each pixel in the original image to the capsule endoscope; step S22, converting the depth image into a second binary image; step S23, obtaining each connected region of bright pixels and counting the total quantity of connected regions with bright pixel quantity greater than a preset second quantity threshold based on the second binary image, where the bright pixels refer to the pixels with far distance; step S24, determining whether the current original image contains a cavity based on the counted total number of connected regions of bright pixels.

For step S21, there are various methods to convert the original image into a depth image, which is a prior art. For more details, please refer to the Chinese patent application No. CN110335318A, titled "Camera System Based Measurement Method for Object in Digestive Tract", cited herein. The depth image can be obtained through the following step: in a calibration phase, a relationship between the brightness of any pixel on a calibration image and the depth distance z between the actual position of the pixel in the simulated digestive tract and the capsule endoscope is obtained, as well as the relationship between the scale r of any pixel on the calibration image and the depth distance z between the actual position of the pixel in the simulated digestive tract and the capsule endoscope. Then, in an actual measurement stage, by obtaining the pixel brightness of each pixel on the original image, the depth image can be obtained through the obtained relationships in the calibration phase.

For step S22, there are various methods to convert the depth image into the second binary image. In one embodiment of the present invention, step S22 specifically comprises: representing the value of a pixel in the second binary image with a third value if the depth value of the pixel in the depth image is greater than a preset depth threshold; representing the value of a pixel in the second binary image with a fourth value if the depth value of the pixel in the depth image is not greater than the depth threshold, where the third value and the fourth value are different.

The preset depth threshold is a depth constant, and the value can be specifically set as needed.

Figure 7:
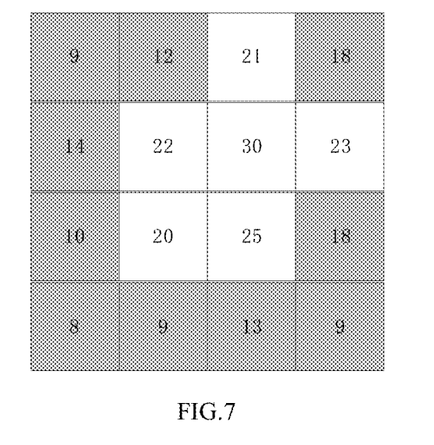
FIG. 7 shows a depth image of a specific embodiment of the present invention.
Figure 8:
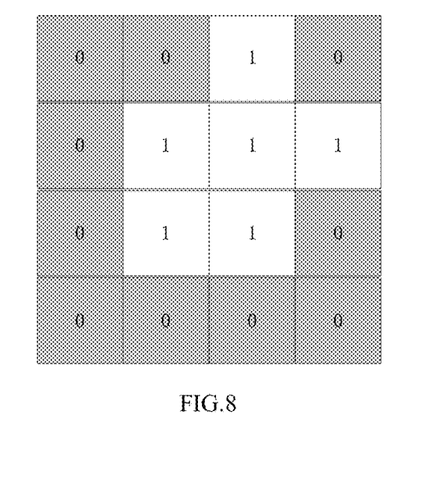
FIG. 8 shows a second binary image of a specific embodiment of the present invention.

Referring to FIG. 7, in a specific embodiment of the present invention, the preset depth threshold is set to 19, in millimeters. Further, by comparing each depth value in the depth image with the preset depth threshold in turn, a second binary image is formed as shown in FIG. 8.

It should be noted that for the second binary image, the depth value of each pixel in the image is replaced by only two values. Accordingly, the two values can be specifically selected as needed. In a specific embodiment of the present invention, the two values are "0" and "1", where "0" represents a smaller depth value of the pixel, and "1" represents a larger depth value of the pixel, indicating a more distant pixel. In other embodiments of the present invention, "0" and "1" is also interchangeable, and the binary values can be changed accordingly, such as changing to "0" and "255", or to other values, without further elaboration.

For step S22, when taking images of the intestinal cavity, the scene has rich layers with objects at varying distances. Therefore, scenes at a farther distance are usually identified as the intestinal cavity, while those at a closer distance are identified as being taken against the intestinal wall. Binarizing can separate the intestinal cavity area. In this specific embodiment, set the value to 1 for distances greater than the preset depth threshold, and set it to 0 for distances less than the depth threshold.

For step S23, the quantity of bright pixels in each connected region of bright pixels is counted, and compared with the second quantity threshold to exclude discrete connected regions of bright pixels. In the depth as shown in FIG. 8, after comparison, the quantity of remaining connected regions of bright pixels used for calculation is 1.

Preferably, for step S24, if the total quantity of connected regions of bright pixels is 0, it is determined that the current original image does not contain cavities; if the total quantity of connected regions of bright pixels is between 0 and a second index threshold, it is determined that that the current original image contains cavities; if the total quantity of connected regions of bright pixels is not less than the second index threshold, it is determined that the current original image is incorrectly identified.

The second index threshold is a constant, and the value can be specifically set as needed. In specific embodiments of the present invention, the number of cavities in the image, if present, is usually 1, 2, or 3, and accordingly, the second index threshold is set to 4, for instance.

It should be noted that the two methods for determining whether the current original image contains a cavity, namely method 1 and method 2, can be performed alternatively, sequentially, or simultaneously. When performed sequentially, starting with method 1 followed by method 2, if method 1 determines that a cavity is present, method 2 is used for verification, and the result of method 2 is considered the final determination. Similarly, when executing method 2 first and then method 1, if method 2 determines that a cavity is present, method 1 is used for verification, and the result of method 1 is considered the final determination. When both methods are executed simultaneously, if both method 1 and method 2 determine that a cavity is present, it is determined that there is a cavity; otherwise, both results indicate that the current original image recognition is incorrect.

Preferably, for step S1, if a cavity is determined to be contained, increasing the frame rate based on the original frame rate, specifically comprising: if it is determined that the current original image contains a cavity, taking the total area of the connected region used to determine the cavity as a cavity index corresponding to the original image; adjusting the frame rate according to the cavity index; where the larger the cavity index, the higher the frame rate.

For ease of understanding, the specific embodiment shown in FIG. 4 is used for explanation, for example, the area of each pixel is represented by 1. In the embodiment as shown in FIG. 4, the connected region of dark pixels contains 6 pixels, so its area can be represented by the value 6. Therefore, the cavity index of the corresponding original image is 6.

Further, a mapping relationship between the frame rate and the cavity index is configured before capturing images. For example, the original base frame rate is 2 fps. When the cavity index is 4, the frame rate is 4 fps; when the cavity index is 5, the frame rate is 5 fps; when the cavity index is 6, the frame rate is 6 fps, and so on. The mapping relationship between the cavity index and the frame rate can be configured according to specific needs, and not be further described here.

In accordance with the above mapping relationship, the specific embodiment shown in FIG. 4 contains a cavity with a cavity index of 6. Therefore, the frame rate needs to be increased and adjusted to 6 fps after the adjustment.

Figure 9:
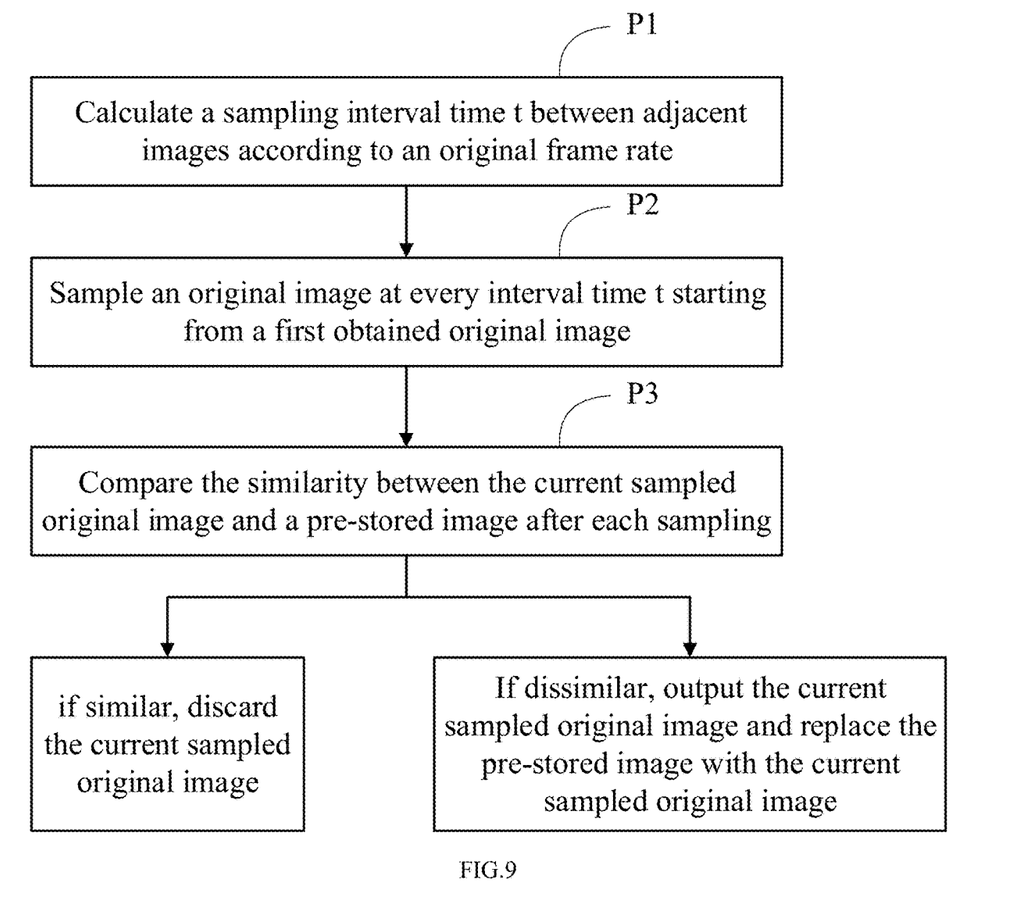
FIG. 9 shows an exemplar process flow diagram of the image processing method in a preferred embodiment based on FIG. 1.

Further, as shown in FIG. 9, in a preferred embodiment of the present invention, after determining whether the current original image contains a cavity, the method further comprises: step P1, calculating a sampling interval time t between adjacent images according to the original frame rate; step P2, sampling an original image at every interval time t starting from the first obtained original image; and step P3, comparing the similarity between the current sampled original image and the pre-stored image after each sampling; if the current sampled original image is similar to the pre-stored image, discarding the current sampled original image; and if the current sampled original image is dissimilar to the pre-stored imaged, outputting the current sampled original image and replacing the pre-stored image with the current sampled original image. Thus, although a large number of redundant images are generated during image capturing, selective output of images is implemented in the output process, avoiding the output of too many repetitive images, thereby improving the efficiency of physicians in review of images and reducing their workload.

It should be noted that the above steps P1 to P3 are merely additional labels for description convenience, and the order of these labels does not represent the execution order of the steps in actual applications.

For step P1, t=1/f(s), where f represents the original frame rate, and s is the time unit "second".

For step P2, the sampling interval time is t, which means that if the original frame rate remains unchanged, every captured image can be sampled. If the frame rate is increased, only the images captured at every interval time t from the first image can be sampled; that is, after increasing the frame rate, the total quantity of samples taken within the same time remains unchanged. In this way, the sampling efficiency is improved.

It should be noted that the sampling means that processing thread samples the captured images at a predetermined time interval, and further, only comparing the similarity of the sampled images. Thus, selectively performing similarity comparisons and further selecting images for output can enhance the efficiency of image review.

For step P3, the similarity comparison is a general algorithm of existing technology; it usually requires feature extraction from the original image, feature vector statistics, and finally similarity judgment.

For example, using an image similarity algorithm based on Local Binary Pattern (LBP), the main steps of the algorithm are: extracting the LBP information of the image, dividing it into multiple regions to calculate histograms, forming feature vectors that describe the image information, and then determining whether two images are similar based on the size of the feature vectors, without further elaboration here.

When a capsule endoscope is capturing images, rotation may occur. To avoid the impact of multi-angle images on similarity assessment and user experience, images can be rotated according to the orientation of the capsule endoscope before similarity comparison, ensuring they have the same shooting angle and posture as the reference image. In this way, the similarity judgment results are more accurate.

Figure 10:
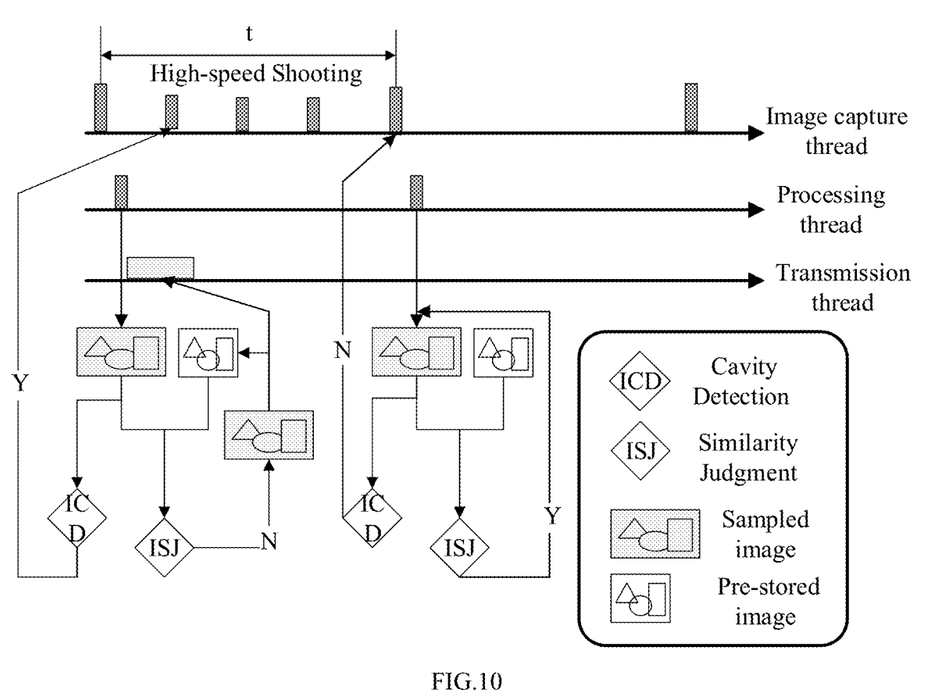
FIG. 10 shows an exemplar process flow diagram of an image-based thread operation, in accordance with an embodiment of the present invention.
Figure 11:
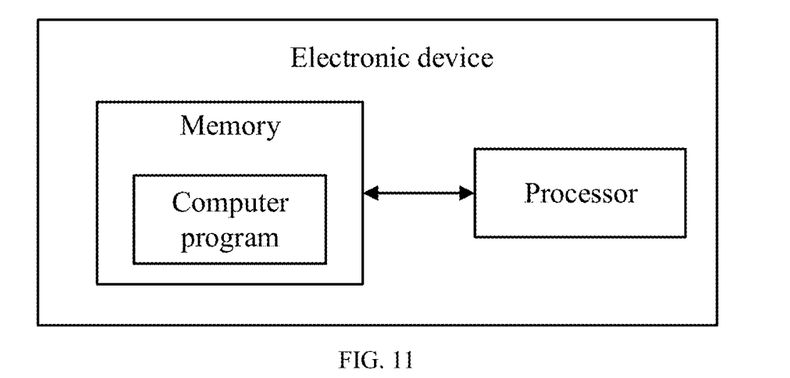
FIG. 11 is a schematic diagram of components of an exemplary electronic device in accordance with the present invention.

As shown in FIG. 10, in a specific embodiment of the present invention, separate threads are used to perform the above steps. Specifically, three independent threads are configured, namely the image capture thread, the processing thread, and the transmission thread, with each thread running independently without interference. In this way, the frame rate can be adjusted according to the cavity, while effectively reducing the transmission of redundant images. At the same time, during the reduction of redundant image transmission, the workload does not increase due to the adjustment of the frame rate.

In detail, the image capture thread captures images at the configured frame rate, and when the cavity is not detected, it always captures images at the original frame rate, that is, one image is captured every interval time t. Meanwhile, the processing thread samples an image every interval time t. After the frame rate increases, the image capture thread captures images according to the adjusted frame rate. In this specific embodiment, the capture frame rate is increased based on the original frame rate, that is, an image is captured every interval time t1, where t1<t. At the same time, the processing thread also samples an image at every interval time t. The columns on the image capture thread represent images, where taller columns indicate sampled images calculated based on the original frame rate.

The transmission thread only compares the similarity between the sampled image and the pre-stored image; the first pre-stored image is the first sampled image, and subsequent pre-stored images are changed based on the similarity results. From the above, it can be seen that here, regardless of whether the cavity is detected or not, the processing thread always samples at an interval time t and performs Intestinal Cavity Detection (ICD) and Image Similarity Judgment (ISJ) on the sampled images through the transmission thread.

Preferably, for step S1, if a cavity is determined to be contained, after increasing the frame rate based on the original frame rate, the method also comprises: calculating the sampling interval time t for adjacent images according to the original frame rate, starting from the first obtained original image, sampling an original image every interval time t; and after each sampling, repeatedly performing step S1, that is, determining whether the current sampled original image contains a cavity.

After identifying a cavity, increasing the frame rate of the image capture thread, but the images obtained from the increased frame rate is not calculated but all transmitted. If no cavity is identified, the frame rate is not changed. Meanwhile, the transmission thread compares the similarity of the sampled images, and when the current image is deemed similar, discard it and do not transmit.

Correspondingly, one branch in the transmission thread performs similarity comparison on the sampled original images and determines whether to output the current sampled original image based on the comparison result; another branch performs cavity identification on the original image and adjusts the frame rate according to the identification result.

Alternatively, in other embodiments of the present invention, the sampling interval time of adjacent images can be calculated based on the increased frame rate, and then the similarity comparison and output of the sampled images can be performed, or the cavity identification of the sampled images can be carried out and the frame rate can be adjusted, without further elaboration here.

Further, the present invention provides an electronic device, comprising a memory and a processor, where the memory stores a computer program that can run on the processor, and the processor executes the computer program to implement the steps of the image processing method.

Further, the present invention provides a computer-readable storage medium which stores a computer program and the computer program is executed by the processor to implement the steps of the image processing method as described above.

In summary, the image processing method, electronic device, and readable storage medium of the present invention can efficiently and simply determine whether the capsule endoscope has reached the preset detection position based on the images obtained from the existing hardware structure, without a need for additional hardware assistance and with low computational requirements for the hardware. Meanwhile, during the image capturing, the images are obtained at an extremely low equivalent frame rate, significantly saving battery power and improving the efficiency of the capsule endoscope.

It should be understood that, although the description is described in terms of embodiments, not every embodiment merely comprises an independent technical solution. The description is described in this manner for clarity, and those skilled in the art should consider the description as a whole, and the technical solutions in each embodiment may also be combined as appropriate to form other embodiments that can be understood by those skilled in the art.

The series of detailed descriptions set forth above are only specific descriptions of feasible embodiments of the present invention and are not intended to limit the scope of protection of the present invention. Equivalent embodiments or modifications made within the spirit of the present invention should be included within the protection scope of the present invention.

The invention claimed is:

1. An image processing method, comprising:
    obtaining an original image of a capsule endoscope, determining whether the current original image contains a cavity; increasing a frame rate based on the original frame rate when the current original image contains a cavity; maintaining the original frame rate for image capturing when the current original image does not contain a cavity,
    converting the current original image into a grayscale image;
    converting the grayscale image into a first binary image;
    obtaining each connected region of dark pixels and counting a total quantity of connected regions with dark pixel quantity greater than a preset first quantity threshold based on the first binary image, wherein the dark pixels refer to the pixels in the grayscale image with grayscale values not greater than a grayscale threshold; and
    determining whether the current original image contains a cavity based on the counted total quantity of connected regions of dark pixels.

2. The image processing method of claim 1, wherein converting the grayscale image to the first binary image comprises: binarizing the grayscale image based on a maximum grayscale value and a minimum grayscale value thereof to form the first binary image.

3. The image processing method of claim 2, wherein binarizing the grayscale image based on the maximum grayscale value and the minimum grayscale value thereof to form the first binary image specifically comprises:
    representing the value of a pixel in the first binary image with a first value when the grayscale value of the pixel in the grayscale image is greater than the grayscale threshold; representing the value of a pixel in the first binary image with a second value when the grayscale value of the pixel in the grayscale image is not greater than the grayscale threshold, wherein the first value and the second value are different;
    wherein the grayscale threshold $m1=R \times maxv+(1-R) \times minv$, R is a coefficient of proportionality, which is a constant; maxv represents the maximum grayscale value in the grayscale image, and minv represents the minimum grayscale value in the grayscale image.

4. The image processing method of claim 1, wherein determining whether the current original image contains a cavity based on the counted total quantity of connected regions of dark pixels specifically comprises:
    determining that the current original image does not contain a cavity if the total quantity of connected regions of dark pixels is 0;
    determining that the current original image contains a cavity if the total quantity of connected regions of dark pixels is between 0 and a first index threshold; and
    determining that the current original image is incorrectly identified if the total quantity of connected regions of dark pixels is not less than the first index threshold.

5. The image processing method of claim 1, wherein determining whether the current original image contains a cavity comprises:
    converting the current original image into a depth image, wherein each depth value in the depth image represents a distance from an examined object corresponding to each pixel in the original image to the capsule endoscope;
    converting the depth image into a second binary image;
    obtaining each connected region of bright pixels and counting a total quantity of connected regions with bright pixel quantity greater than a preset second quantity threshold based on the second binary image, wherein the bright pixels refer to pixels in the depth image with a depth value greater than a preset depth threshold; and
    determining whether the current original image contains a cavity based on the counted total quantity of connected regions of bright pixels.

6. The image processing method of claim 5, wherein converting the depth image into the second binary image comprises:
    representing the value of a pixel in the second binary image with a third value if the depth value of the pixel in the depth image is greater than the depth threshold;
    representing the value of a pixel in the second binary image with a fourth value if the depth value of the pixel in the depth image is not greater than the depth threshold, wherein the third value and the fourth value are different.

7. The image processing method of claim 5, wherein determining whether the current original image contains a cavity based on the counted total quantity of connected regions of bright pixels specifically comprises:
    determining that the current original image does not contain a cavity if the total quantity of connected regions of bright pixels is 0;
    determining that the current original image contains a cavity if the total quantity of connected regions of bright pixels is between 0 and a second index threshold; and
    determining that the current original image is incorrectly identified if the total quantity of connected regions of bright pixels is not less than the second index threshold.

8. The image processing method of claim 1, wherein increasing the frame rate based on the original frame rate when the current original image contains a cavity, specifically comprises:
    taking a total area of the connected region used to determine the cavity as a cavity index corresponding to the original image if it is determined that the current original image contains a cavity;

adjusting the frame rate according to the cavity index, wherein the larger the cavity index, the higher the frame rate.

9. The image processing method of claim 1, wherein after increasing the frame rate based on the original frame rate, the method further comprises:
   calculating a sampling interval time t between adjacent images according to the original frame rate;
   sampling an original image at every interval time t starting from the first obtained original image; and
   determining whether the original image contains a cavity based on the current sampled original image after each sampling.

10. The image processing method of claim 1, wherein after determining whether the current original image contains a cavity, the method further comprises:
    calculating a sampling interval time t between adjacent images according to the original frame rate;
    sampling an original image at every interval time t starting from the first obtained original image; and
    comparing the similarity between the current sampled original image and a pre-stored image;
    discarding the current sampled original image if the current sampled original image is similar to the pre-stored image; and
    outputting the current sampled original image and replacing the pre-stored image with the current sampled original image if the current sampled original image is dissimilar to the pre-stored imaged.

11. An electronic device, comprising a memory and a processor, wherein the memory stores a computer program that runs on the processor, and the processor executes the computer program to implement steps of an image processing method, wherein the image processing method comprises:
    obtaining an original image of a capsule endoscope, determining whether the current original image contains a cavity; increasing a frame rate based on the original frame rate when the current original image contains a cavity; maintaining the original frame rate for image capturing when the current original image does not contain a cavity,
    converting the current original image into a grayscale image;
    converting the grayscale image into a first binary image;
    obtaining each connected region of dark pixels and counting a total quantity of connected regions with dark pixel quantity greater than a preset first quantity threshold based on the first binary image, wherein the dark pixels refer to the pixels in the grayscale image with grayscale values not greater than a grayscale threshold; and
    determining whether the current original image contains a cavity based on the counted total quantity of connected regions of dark pixels.

12. A non-transitory computer-readable storage medium having stored thereon a computer program that, when executed by a processor, implements steps of an image processing method, wherein the image processing method comprises:
    obtaining an original image of a capsule endoscope, determining whether the current original image contains a cavity; increasing a frame rate based on the original frame rate when the current original image contains a cavity; maintaining the original frame rate for image capturing when the current original image does not contain a cavity,
    converting the current original image into a grayscale image;
    converting the grayscale image into a first binary image;
    obtaining each connected region of dark pixels and counting a total quantity of connected regions with dark pixel quantity greater than a preset first quantity threshold based on the first binary image, wherein the dark pixels refer to the pixels in the grayscale image with grayscale values not greater than a grayscale threshold; and
    determining whether the current original image contains a cavity based on the counted total quantity of connected regions of dark pixels.

* * * * *